(12) United States Patent
Gielen et al.

(10) Patent No.: US 6,312,469 B1
(45) Date of Patent: Nov. 6, 2001

(54) LAMINA PROSTHESIS FOR DELIVERY OF MEDICAL TREATMENT

(75) Inventors: Frans L. H. Gielen, Eckelrade; Henricus M. P. Knuth, Kerkrade, both of (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/394,352

(22) Filed: Sep. 13, 1999

(51) Int. Cl.[7] ..................................................... A61F 2/44
(52) U.S. Cl. ......................................................... 623/17.11
(58) Field of Search ............................. 606/61; 623/17.16

(56) References Cited

U.S. PATENT DOCUMENTS

| | | | |
|---|---|---|---|
| 4,313,438 | 2/1982 | Greatbatch | 128/207.21 |
| 4,683,896 | 8/1987 | Herbst et al. | 128/785 |
| 4,955,908 | * 9/1990 | Frey et al. | 623/17.16 |
| 5,330,477 | 7/1994 | Crook | 606/69 |
| 5,484,445 | 1/1996 | Knuth | 606/129 |
| 5,674,296 | * 10/1997 | Bryan et al. | 623/17.16 |
| 6,120,502 | * 9/2000 | Michelson | 606/61 |

* cited by examiner

Primary Examiner—David J. Isabella
(74) Attorney, Agent, or Firm—Thomas F. Woods; Thomas G. Berry

(57) ABSTRACT

A prosthetic lamina that replaces a portion of the lamina bone structure. The prosthetic lamina may be configured to deliver a variety of medical therapies, such as electrodes for electrical stimulation, fluid channels for delivering drugs, catheters for dispensing drugs and various systems for healing bone tissue.

5 Claims, 5 Drawing Sheets

LAMINA PROSTHESIS FOR DELIVERY OF MEDICAL TREATMENT

FIELD OF THE INVENTION

This invention relates to implantable techniques for delivering medical treatment, such as electrical stimulation or drugs, to the spinal cord. More particularly, this invention relates to a prosthetic lamina that may replace a portion of the lamina bone structure to help support deteriorating bone structure. The present invention may additionally be configured with various means for electrical stimulation, such as electrodes, and various means to deliver other types of medical treatment, such as fluid channels or catheters for dispensing drugs.

BACKGROUND OF THE INVENTION

The spinal cord has typically been difficult to treat medically because it is not easily accessible and its vital function in the body demands that techniques used for medical treatment disturb the function of the cord minimally or not at all. However, medical treatment of the spinal cord may be necessary for a number of reasons, such as to alleviate pain, to control certain aspects of the nervous system, to replace deteriorating structure or to treat disease. Several techniques have been developed to treat the spinal cord, depending on the type of treatment required.

For example, electrical stimulation of a spinal cord, is one well-known technique in the art. Such electrical stimulation in the spinal cord has been shown to be effective in relieving certain types of pain. Selective nerve stimulation has also been used to control various aspects of the nervous system for such objects as controlling urination, fecal incontinence or penile erection.

Techniques are also known in the field of reconstructive surgery to replace the deteriorating bone structure of the vertebral canal with prosthetic structures, such as a prosthetic lamina. In one surgical procedure, called a laminectomy, the tissue is spread away from around the cord and the ligaments between two bony vertebral elements are cut. Then all or part of one section of the lamina is removed and replaced by a prosthetic apparatus. The prosthetic is secured to the remaining bone and provides additional support.

Furthermore, some techniques, such as that provided in U.S. Pat. No. 4,313,438 to Greatbatch and U.S. Pat. No. 5,330,477 to Crook, both of which are incorporated herein by reference, show that electrical stimulation of bone tissue can accelerate the growth of the tissue, create a germicidal environment for curing tissue and bone infections and may inhibit the growth of tumors.

Delivery of drugs to the spinal cord for such purposes as creating a germicidal environment or relieving pain is also desirable. For example, in one technique, a small hole is drilled in the bony cylinder of the spinal cord and a catheter is placed into the hole through the bone and through the dura mater towards the side of the cord that is affected by pain. Pain-relieving drugs may then be delivered through the catheter. Spasticity-relieving drugs may be similarly delivered.

Successful or beneficial electrical stimulation and drug delivery to the spinal cord remain difficult to achieve because of the cord's location and function.

A lead may be implanted adjacent the spinal cord to provide stimulation, such as described in U.S. Pat. Nos. 4,285,347; 5,121,754; 5,501,703; 5,628,317; and 5,643,330; all of which are incorporated herein by reference in their respective entireties. It may be difficult to implant such leads in the proper location. Over time, particularly in the first two or three weeks following lead implantation, the position of the lead with respect to the spinal cord may change inadvertently and in an undesirable manner. Because of such displacement, the lead may not provide stimulation to the precise target spinal area where it was originally implanted. Such positioning changes may impair the clinical benefit of the stimulation provided by the lead.

Another technique is disclosed in U.S. Pat. No. 5,484,445 to Knuth, incorporated herein by reference in its entirety, where stimulation electrodes are anchored directly to the bone. Problems such as tearing of the bone tissue may occur when the electrodes or leads are directly fixed to the bone. The techniques of Greatbatch and Crook described above also require that electrical components be anchored directly to the remaining bone tissue.

Similar difficulties are faced in delivering drugs to or near the spinal cord. A chronically implanted catheter may change position as the patient in which it is implanted moves or may not stay in place because the patient in whom it is implanted has poor posture. However, if a catheter is anchored to the bone, there exists the danger of damaging bone tissue. Finally, drilling a hole to insert a catheter or to create an opening for drug delivery may lead to bone damage, particularly if the bone is already in the process of deteriorating.

In the case of many patients requiring spinal cord treatment, the bony elements of the cord are in such a deteriorated state that it is detrimental to anchor any element to the bone. Because most medical treatment of the spinal cord is intensive and may last over several weeks or even years, the patient may be forced to lie still while electrical stimulation is performed or while drugs are dispensed through an implanted catheter.

Other disclosures relating to prosthetic vertebral elements include the U.S. Patents listed below in Table 1.

| U.S. Pat. No. | Title |
| --- | --- |
| 5,562,736 | Method for Surgical Implantation of a Prosthetic Spinal Disc Nucleus |
| 5,147,404 | Vertebra Prosthesis |
| 4,554,914 | Prosthetic Vertebral Body |
| 4,401,112 | Spinal Fixator |
| 4,369,769 | Spinal Fixation Device and Method |
| 4,141,365 | Epidural lead electrode and insertion needle |
| 3,978,499 | Surgical Implant and Method for its Production |

As those of ordinary skill in the art will appreciate readily upon reading the Summary of the Invention, Detailed Description of the Preferred Embodiments and claims set forth below, at least some of the devices and methods disclosed in the patents of Table 1 and elsewhere above may be modified advantageously by using the teachings of the present invention.

It would be desirable therefore to provide a structure that can remain appropriately placed for effective delivery of medical treatment to a spinal cord over a reasonable period of time, even if the patient is mobile. It would also be desirable to provide a structure to which components for effective medical treatment may be anchored without causing further damage to a spinal cord. It would also be desirable to provide a structure capable of delivering a variety of treatments to the spinal cord, depending on the needs of the individual patient.

SUMMARY OF THE INVENTION

The lamina prosthesis of the present invention overcomes at least some of the disadvantages of the prior art by providing a prosthesis that is capable of providing support to deteriorating bone structure, while at the same time being capable of delivering a variety of medical treatments.

Various embodiments of the lamina prosthesis of the present invention have certain objects. That is, various embodiments of the present invention provide solutions to certain problems existing in the prior art, such as one or more of: (a) the need to use one structure to deliver drugs to the spinal cord and a different structure to deliver electrical stimulation; (b) the need to implant one device to support deteriorating structure, a different device to provide stimulation, and yet another device to deliver drugs, depending on the individual patient's condition; and (c) the need to introduce devices for treatment adjacent the spinal cord which may not be located in the most effective locations or which may migrate away from the optimal location.

Various embodiments of the lamina prosthesis of the present invention provide certain advantages, including one or more of: (a) the capability to be implanted and remain stable in an optimal position for delivery of stimulation or drugs in relation to the spinal cord; (b) the capability to be placed in position to treat the spinal cord without requiring anchoring to the bone that might further degrade the bone; and (c) the ability to perform the function of supporting or stabilizing bone structure, the function of providing stimulation to the cord and the function of delivering drugs to the cord at the same time so that more than one medical treatment may be delivered to the spinal cord of a single patient.

Various embodiments of the lamina prosthesis of the present invention have certain features; including one or more of: (a) a substantially integral prosthesis capable of supporting or stabilizing bone structure of the spinal cord; (b) a prosthetic device which may be customized with a variety of medical delivery components, such as a variety of electrodes or a variety of fluid channels, depending on the needs of the individual patient; (c) a prosthetic device which may deliver a variety of treatments simultaneously; and (d) a prosthetic device that is placed in a natural position to deliver treatment to the spinal cord owing to its structure mimicing the natural structure of a component of the spinal cord.

Methods of making and using the lamina prosthesis described above also fall within the scope of the invention.

Other features, advantages and objects of the present invention will become more apparent by referring to the appended drawings, detailed description and claims.

DETAILED DESCRIPTION OF THE PREFERRED EMBODIMENTS

Figure 1:
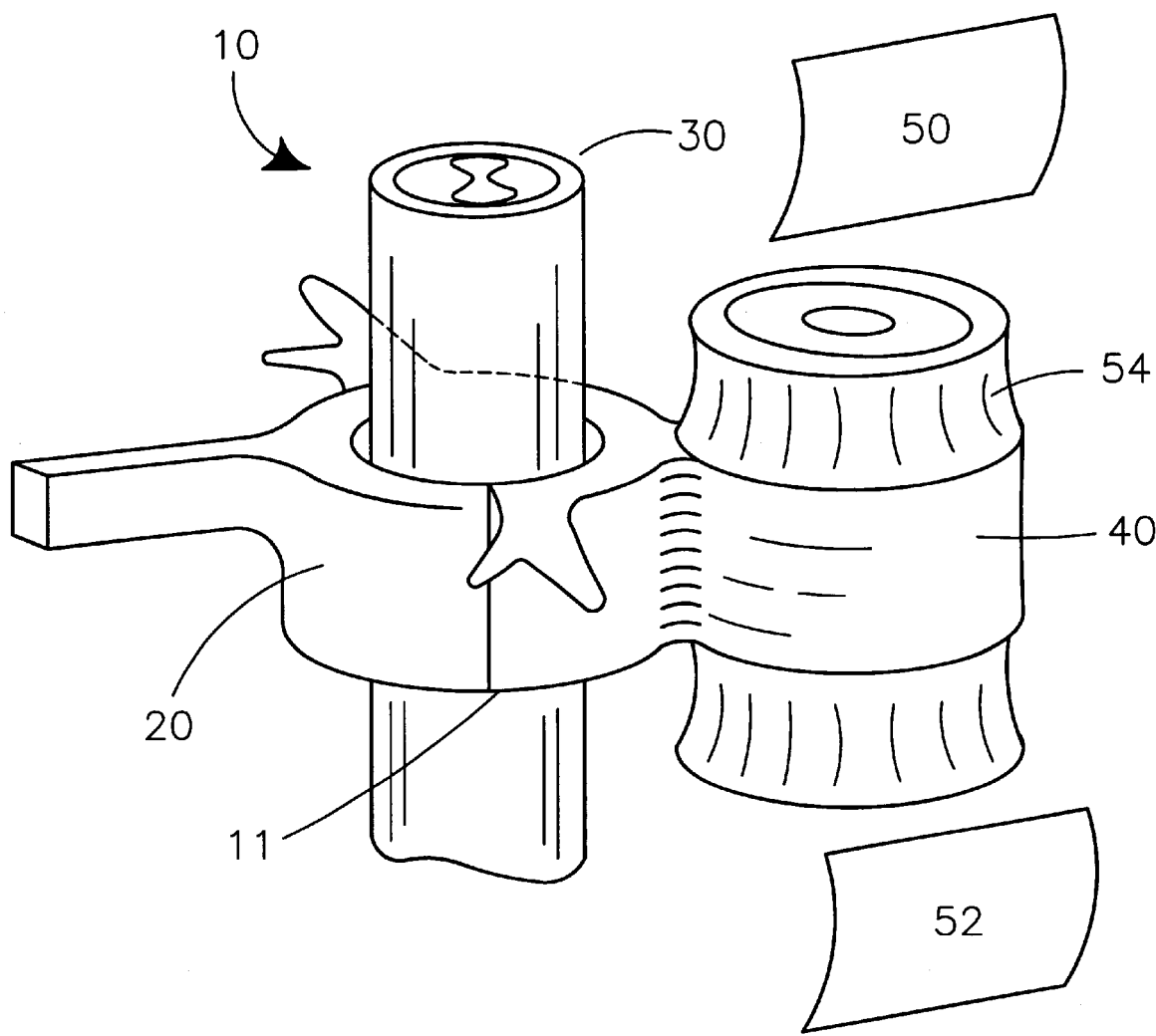
FIG. 1 is a perspective view of one embodiment of the prosthetic lamina apparatus of the present invention, comprising a body portion and support means.
Figure 2:
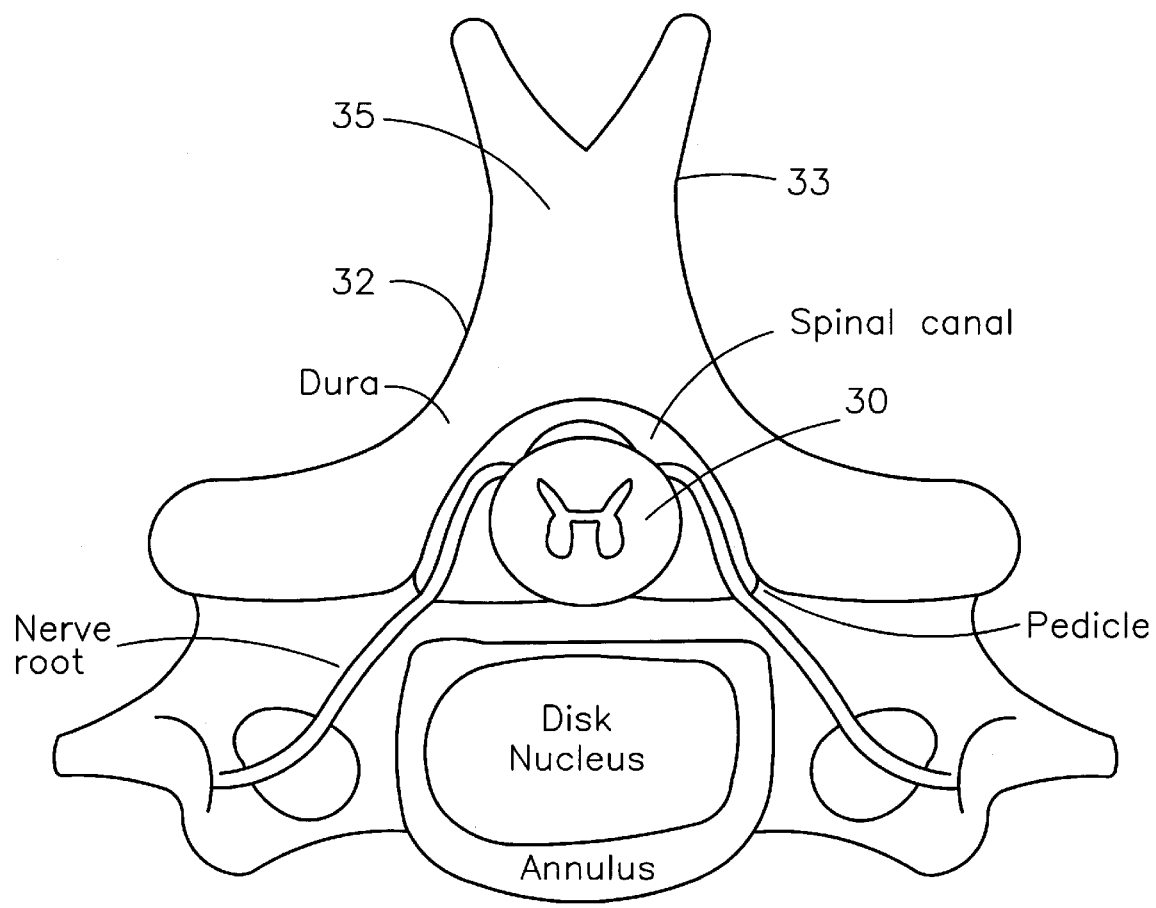
FIG. 2 is a bottom sectional view of a vertebra and disk.

One embodiment of prosthetic lamina apparatus 10 of the present invention is shown in FIG. 1. Referring to FIG. 2, bottom views of a vertebra and disk are shown for purposes of comparison. The spinal cord is indicated at 30 and the lamina is indicated at 32. Prosthetic lamina apparatus 10 of the present invention may replace all or a portion of lamina 32. Lamina 32 extends generally towards the back of a typical vertebrate. Lamina 32 has spinous process 33 and an inferior articular process (not shown) which extend downwardly to form arch-like structure 35.

Figure 3:
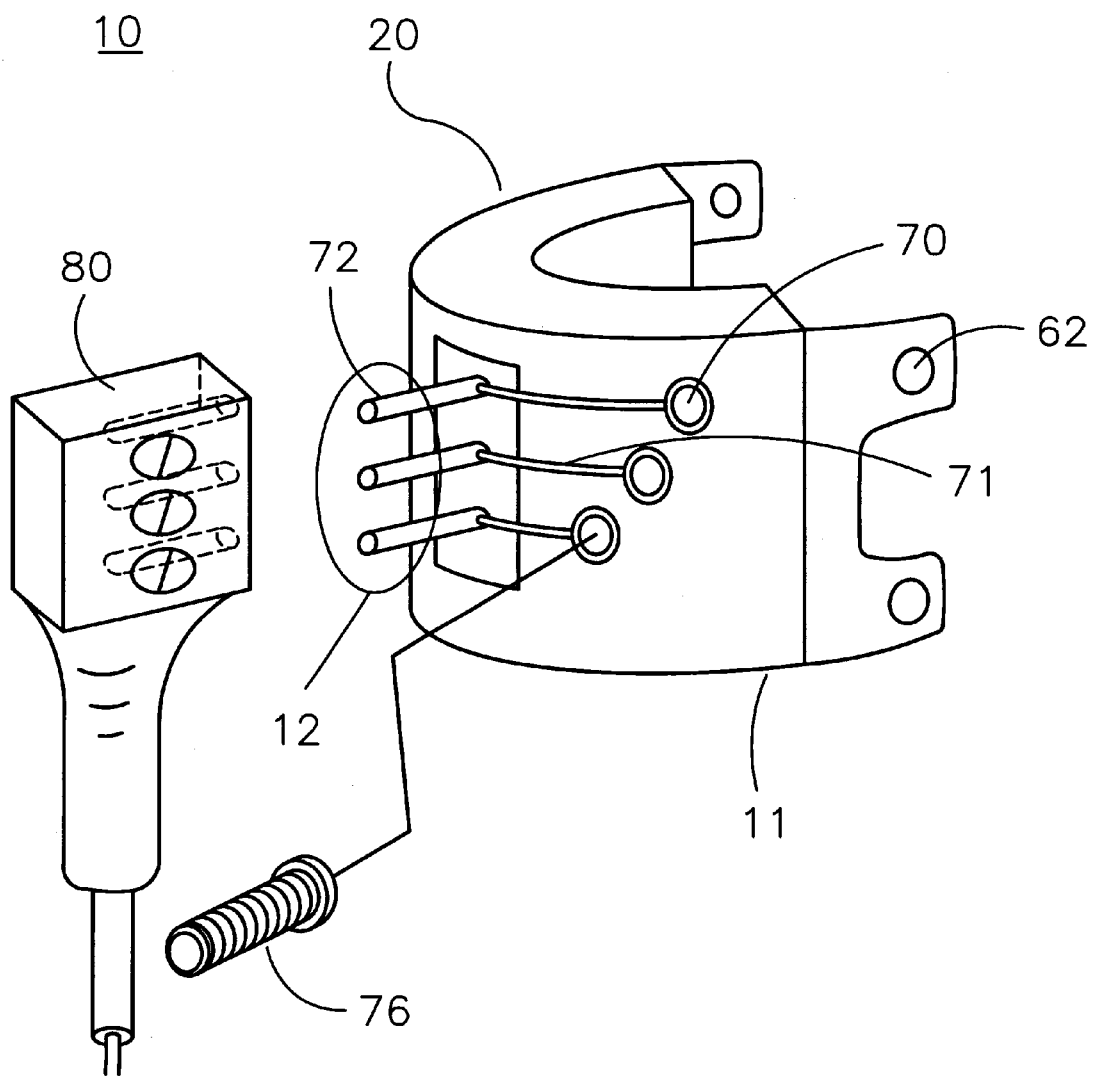
FIG. 3 is a perspective view of another embodiment of the present invention.

Referring now to FIGS. 1 and 3, one embodiment of the prosthetic lamina apparatus of the present invention for delivering treatment to the spinal cord is shown and comprises prosthetic lamina 11 and delivery treatment system 12 operatively attached thereto. Prosthetic lamina 11 is inserted adjacent the spinal cord and treatment is delivered therethrough. Prosthetic lamina 11 preferably includes support means 40 attached to body 20 by standard biocompatible means such as, for example, surgical glue, biocompatible rubber or suturing. Alternatively, support means 40 and body 20 may be formed as one integral member. Preferably, prosthetic lamina apparatus 10 is configured to conform comfortably to spinal cord 30.

In the embodiment of the present invention shown in FIG. 1, body 20 and support means 40 are preferably formed so that when fitted together body 20 and support means 40 functionally resemble a naturally occurring lamina, such as the one shown at 32 in FIG. 2. Support means 40 may be adjustable and is preferably located within the cavity between two healthy vertebral bodies 50, 52 that adjoin the vertebral body 54, the lamina of which is in the process of being replaced by prosthetic lamina 11. Furthermore, and if necessary for additional support, support means 40 may be secured to one or more of healthy vertebral bodies 50, 52 or to the remaining body elements of the vertebral body 54, the lamina of which is in the process of being replaced by prosthetic lamina 11. The means of securing those elements may include, for example, a quantity of conventional bonding composition and/or glue (adhesive) located on the surface of vertebra body 50, 52, 54 or prosthetic lamina 11 and/or one or more throughholes in the vertebra body or element to permit tissue, muscle and the like to be sutured directly to support means 40. Any type of bonding composition or adhesive may be used, provided it has sufficient bonding ability and no significantly detrimental effect on the present system or the individual being treated. Other means may be employed to secure the support means 40 such as mechanical means, wires, rods and the like.

In employing the embodiment of the present invention shown in FIG. 3, a window-like portion of natural lamina 32 is removed. Body 20 of prosthetic lamina 11 may then be plugged into the window that has been created in lamina 32. It is preferred that body 20 be positioned appropriately when lamina holes 62 are drilled therethrough for alignment with screw holes 62. Appropriate screws (not shown) may then be inserted. Other attachment means such as some of those described above may also be used. One method that may be adapted to attach prosthetic lamina 11 and to anchor a component such as lead 64 incorporated into body 20 is described more fully in U.S. Pat. No. 5,484,445 hereby incorporated herein by reference in its entirety.

Figure 4:
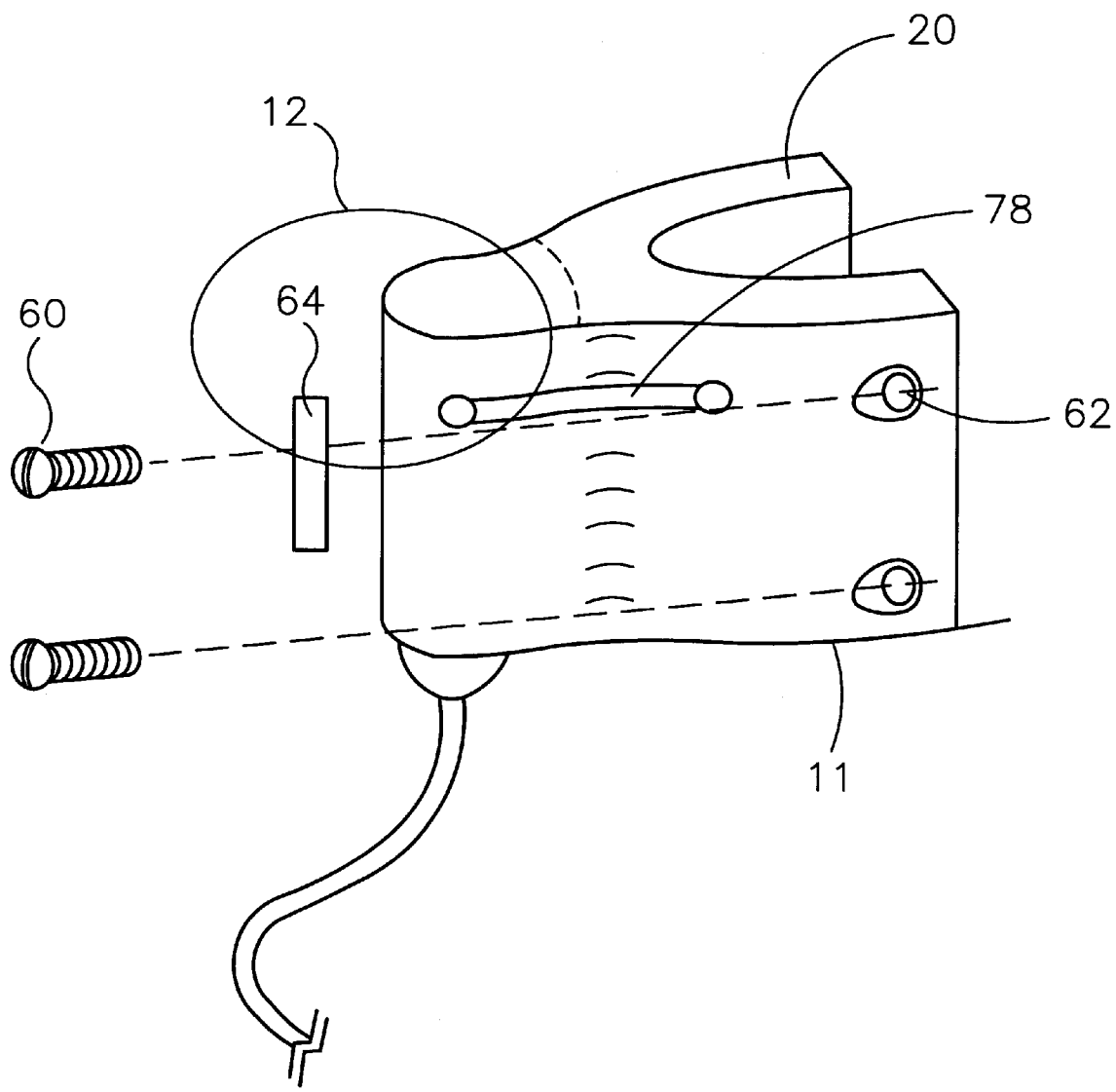
FIG. 4 is a perspective view of another embodiment of the present invention.

Referring now to FIG. 4, a second embodiment of body 20 of prosthetic lamina 11 of the present invention is shown. Body 20 of prosthetic lamina 11 may then be attached to support means 40 using attachment means, such as screws 60 (although any of the attachment means described above may be used). Preferably body 20 is positioned appropriately in respect of support means 40 and holes are drilled therethrough to align with screw holes 62.

Prosthetic lamina 11 may be made of any suitable biocompatible, biostable material. A biocompatible material preferably prompts little allergenic response from a patient's body and is resistant to corrosion resulting from being implanted within a human body. Such materials should not cause any additional stress to a patient's body. Body 20 and support means 40 may be made of the same or different biocompatible materials, depending on the configuration of the individual prosthetic lamina 11.

The materials employed to construct prosthetic lamina 11 (including body 20 and/or support means 40) should be capable of enduring the stresses and environment to which such a prosthesis is subjected. In addition, such materials should be substantially chemically inert to not cause any substantial detrimental effect to the individual in whom the prosthesis is implanted. Examples of such materials include various metals and polymeric materials well known in the art.

In one embodiment of the present invention, prosthetic lamina 11 is preferably made of epoxy. Prosthetic lamina 11 may also be made from any standard grade medical material. Prosthetic lamina 11 may replace the lamina bone structure in a vertebrate, particularly in a human patient whose lamina bone structure has been removed by a laminectomy. If prosthetic lamina 11 is configured to include an electrical treatment system, it is preferably made of a material that allows for electronics to be included in the structure of the prosthesis, such as, for example, ceramic.

As seen in FIG. 3, body 20 may include openings 70 lying in the same plane as body 20. Alternatively, openings 70 may be located in any plane of orientation, depending on the treatment intended to be delivered through prosthetic lamina 11. Support means 40 may also include openings (not shown) lying in the same plane as body 20 or in any plane of orientation, depending on the treatment intended to be delivered through prosthetic lumina 11.

Openings 70 allow prosthetic lamina apparatus 10 to be customized for medical treatment of an individual patient. By replacing openings 70 with a variety of treatment components, prosthetic lamina apparatus 10 is optimally configured to treat the spinal cord. Furthermore, and as shown in FIG. 3, treatment components such as wiring 74 may be integrated directly into prosthetic lamina apparatus 10.

As further seen in FIG. 3, prosthetic lamina apparatus 11 may be configured with connector pins 72 to replace one or more of openings 70. Those connector pins may be used to connect prosthetic lamina 11 to a variety of devices, including, but not limited to, implantable pulse generator 80, electronic switch boxes, tubing of various sorts, and drug pumps.

As further seen in FIG. 3, prosthetic lamina apparatus 10 may be configured with electrodes, such as screw adjustable electrode 76, to replace one or more of openings 70. Electrodes 76 may be formed of biocompatible material, such as silver, stainless steel, titanium or platinum. Electrodes 76 may be employed to deliver a variety of medical treatments, such as pain relief promoting healing of bone tissue.

In one embodiment of prosthetic lamina apparatus 10 of the present invention, electrodes 76 may be incorporated into an electrode system that comprises one or more treating electrodes in the form of a electrode adapted to be placed in operative contact with a living tissue site to be healed. Such a treating electrode may release ions that create a germicidal environment, and may further release sufficient number of ions to create a biogalvanic couple for promoting healing of the living bone tissue. Reference is made to U.S. Pat. No. 4,313,438 to Greatbatch which describes this technique more fully, and which is hereby incorporated by reference herein in its entirety.

In another embodiment of prosthetic lamina apparatus 10 of the present invention, electrodes 76 may be incorporated into an electrode system that comprises one or more stimulating electrodes to create a pattern of stimulation. Such a pattern of stimulation may be used to relieve pain. Reference is made to U.S. Pat. Nos. 4,285,347; 5,121,754; 5,501,703; 5,628,317; and 5,643,330; all of which are incorporated herein by reference, each in its respective entirety. Those patents describe a variety of stimulation systems and electrode configurations that may be employed in conjunction with the prosthesis of the present invention.

Preferably, the electrode system of the present invention may further comprises means for establishing an electrical current flow path through the electrodes. Such means may include a direct voltage source in the form of a battery, for example an implantable grade lithium-iodine battery hermetically sealed for use in the body. Other means for establishing an electrical current flow path may include an implantable pulse generator coupled to another suitable source of electrical power.

Although two stimulating systems are provided above by way of example, it will now become apparent to those skilled in the art that prosthetic lamina apparatus 10 of the present invention may be configured with a variety of electrical stimulatory and power delivery systems.

As shown in FIG. 4, prosthetic lamina apparatus 10 may also be configured with fluid channels 78 to replace one or more of openings 70. Fluid channels 78 may be formed of any suitable biocompatible material. Fluid channels 78 may be employed to deliver a variety of medical treatments such as, drugs to relieve pain. In at least one embodiment of the present invention, catheters (not shown) are inserted through fluid channels 78 to deliver medical treatment in accordance with methods well known in the art, such as those employed in intrathecal drug delivery techniques for controlling spasticity. It will now become apparent to those skilled in the art that prosthetic lamina apparatus 10 of the present invention may be configured with a variety of drug delivery systems. Additionally, various components or portions of the apparatus of the present invention are preferably, although not necessarily, NMR compatible.

Although various embodiments of drug delivery systems of the present invention are described above by way of example, it will now become apparent to those skilled in the art that prosthetic lamina apparatus 10 of the present invention may be configured with a variety of drug delivery systems not necessarily disclosed explicitly herein but which are, nevertheless, contemplated in the present invention.

Figure 5:
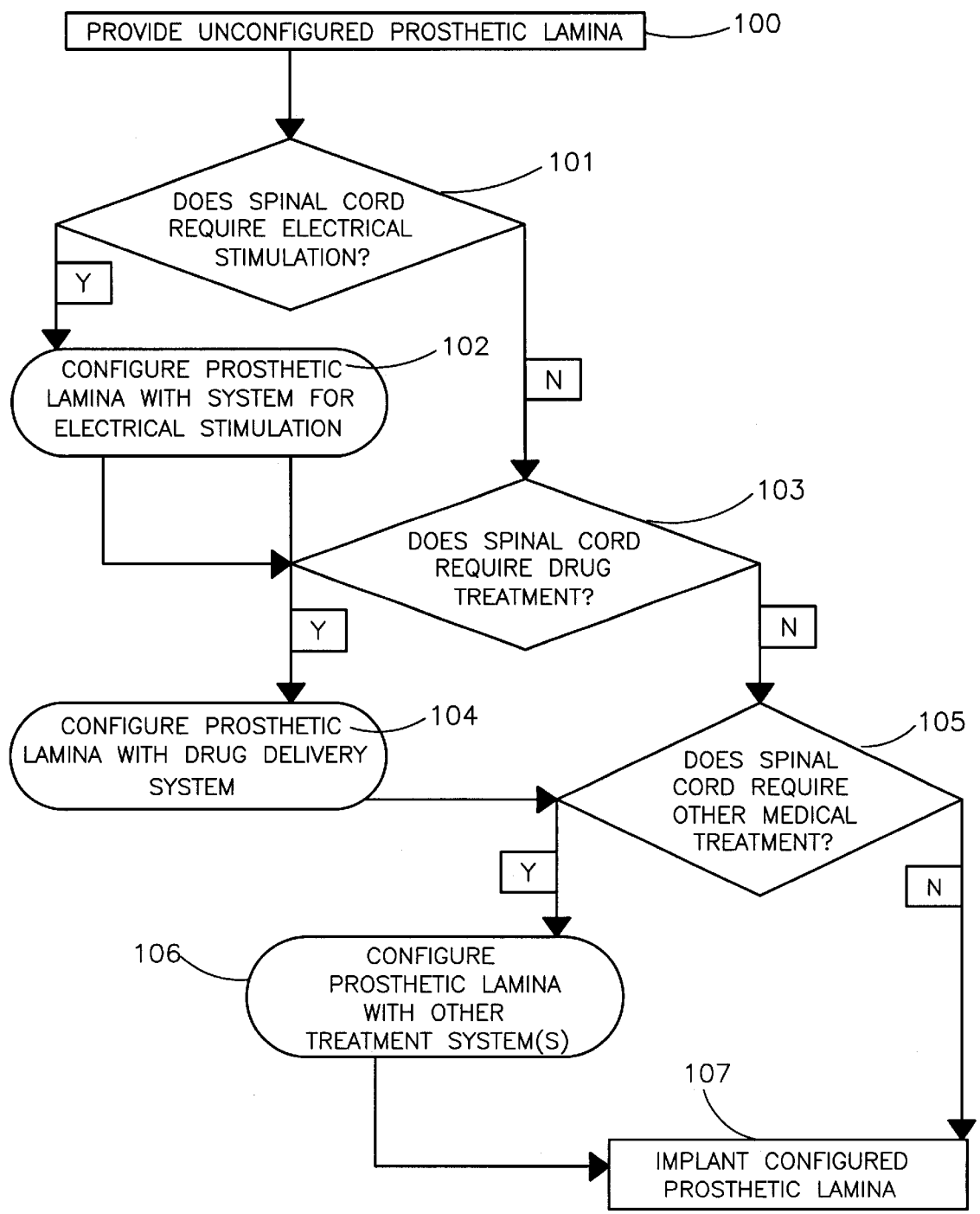
FIG. 5 is a flow diagram showing one method of the present invention.

Referring now to FIG. 5, a flow diagram of steps taken in using lamina prosthetic apparatus 10 to deliver medical treatment according to one method is shown by way of example. Lamina prosthetic apparatus 10 described above is provided at step 100. The patient is evaluated and necessary treatment is determined as, for example at steps 101, 103 or 105. Next, lamina prosthetic apparatus 10 is configured appropriately according to the requirements of the treatment delivery system selected. If at step 101, for example, it is determined that the patient requires treatment in the form of electrical stimulation of the spinal cord, then lamina prosthetic apparatus 10 is appropriately configured with a system for delivering such stimulation (shown at step 102). Alternatively or simultaneously, it may be determined the patient requires drug treatment (shown at step 103). If so, then as shown at 104, lamina prosthetic apparatus 10 is appropriately configured to deliver drugs to the spinal cord. Steps 105 and 106 may be repeated as many times as necessary to configure lamina prosthetic apparatus 10 appropriately in an individual patient. Finally, and as shown at step 107, lamina prosthetic apparatus 10 is appropriately configured and implanted in the patient.

All patents and printed publications cited or referenced hereinabove are hereby incorporated by reference into the specification hereof, each in its respective entirety.

Although specific embodiments of the invention have been set forth herein in some detail, it is to be understood that this has been done for the purposes of illustration only, and is not to be taken as a limitation on the scope of the invention as defined in the appended claims. It is to be understood that various alternatives, substitutions and modifications may be made to the embodiment describe herein without departing from the spirit and scope of the appended claims.

In the claims, means-plus-function clauses are intended to cover the structures described herein as performing the recited function and not only structural equivalents but also equivalent structures. Thus, although surgical glue and a screw may not be structurally similar in that surgical glue employs chemical bonds to fasten biocompatible components together, whereas a screw employs a helical surface, in the environment of fastening means, surgical glue and a screw are equivalent structures.

We claim:

1. A multiple function prosthetic lamina configured for implantation adjacent to a spinal cord and an intermediate vertebral bone structure of a patient, the lamina comprising:

means for at least one of mechanically stabilizing and mechanically supporting the intermediate vertebral bone structure, the stabilizing and supporting means comprising a body and a support means, the body being configured to replace at least a portion of the intermediate vertebral bone structure of the patient when implanted between an upper vertebral bone structure and a lower vertebral bone structure of the patient, the support means being configured to at least partially surround and provide protection to the spinal cord, the body and support means being configured for operable attachment to one another, means for delivering at least one of a drug therapy and an electrical stimulation therapy to at least one of a portion of the patient's spinal cord and a portion of the intermediate vertebral bone structure, the therapy delivery means being at least partially integrated into or forming a portion of the prosthetic lamina, the therapy delivery means further being configured to deliver the at least one therapy to at least one of the spinal cord and the intermediate vertebral bone structure.

2. The prosthetic lamina apparatus of claim 1, wherein the body and the support means are formed as one integral piece.

3. The prosthetic lamina apparatus of claim 1, wherein the delivery treatment system comprises a plurality of electrodes.

4. The prosthetic lamina apparatus of claim 1, wherein the delivery treatment system comprises a system of drug delivery channels.

5. The prosthetic lamina apparatus of claim 1, wherein the delivery treatment system comprises a combination of electrodes and drug delivery channels.

* * * * *